United States Patent [19]

Tomoff et al.

[11] Patent Number: 5,194,226
[45] Date of Patent: Mar. 16, 1993

[54] DOSING DEVICE FOR ANALYZING APPARATUS

[75] Inventors: Toma Tomoff; Wolfgang Chlosta; Viktor Löchle; Henry Klemm, all of Überlingen, Fed. Rep. of Germany

[73] Assignee: Bodenseewerk Perkin-Elmer GmbH, Uberlingen, Fed. Rep. of Germany

[21] Appl. No.: 598,492

[22] Filed: Oct. 16, 1990

[30] Foreign Application Priority Data

Oct. 18, 1989 [DE] Fed. Rep. of Germany ....... 3934699

[51] Int. Cl.[5] .................... B01L 3/02; G01N 33/00; G01N 35/06
[52] U.S. Cl. ...................................... 422/100; 422/73; 73/864.21; 73/864.23; 73/864.25
[58] Field of Search ............... 73/864, 864.02, 864.03, 73/864.21, 864.23, 864.24, 864.25; 422/72, 100

[56] References Cited

U.S. PATENT DOCUMENTS

| | | | |
|---|---|---|---|
| 3,530,721 | 9/1970 | Hrdina | 73/863.72 |
| 3,604,267 | 9/1971 | Johns | 73/864.82 |
| 3,797,318 | 3/1974 | Palm | 73/863.21 |
| 4,094,196 | 6/1978 | Friswell | 73/864.21 |
| 4,242,909 | 1/1981 | Gundelfinger | 73/864.21 |
| 4,286,637 | 9/1981 | Wilson | 141/374 |
| 4,294,126 | 10/1981 | Tomoff et al. | 73/864.21 |
| 4,312,591 | 1/1982 | Tomoff | 356/315 |
| 4,393,726 | 7/1983 | Tamm et al. | 73/864.84 |
| 4,413,534 | 11/1983 | Tomoff et al. | 73/864.21 |
| 4,443,105 | 4/1984 | Huber et al. | 356/312 |
| 4,444,066 | 4/1984 | Ogle et al. | 73/863.72 |
| 4,484,483 | 11/1984 | Riegger et al. | 73/864.23 |
| 4,539,855 | 9/1985 | Jacobs | 73/864.25 |
| 4,558,603 | 12/1985 | Chlosta et al. | 73/864.21 |
| 4,620,452 | 11/1986 | Seki | 73/864.21 |
| 4,705,667 | 11/1987 | Marsoner et al. | 422/68.1 |
| 4,713,974 | 12/1987 | Stone | 73/864.23 |
| 4,888,998 | 12/1989 | Buzza et al. | 73/864.21 |
| 4,939,943 | 7/1990 | Strohmeier | 73/864.21 |
| 4,980,296 | 12/1990 | Trisciani et al. | 436/161 |

Primary Examiner—Robert J. Warden
Assistant Examiner—Christopher Y. Kim
Attorney, Agent, or Firm—Edwin T. Grimes

[57] ABSTRACT

In a dosing device for analyzing apparatus, particulary for liquid chromatography, with a dosing loop, a change-over valve and a dosing needle (20) which can be introduced into a sample inlet (56) of the change-over valve (24), through which dosing needle (20) sample liquid can be dosed by means of a sample pump (66) into the sample inlet (56) and the dosing loop (22), the dosing needle (20) has a conical sealing surface (138) at its front end. The sample inlet (56) has a sample inlet passage (128) which forms a conical annular shoulder (136). The dosing needle (20) with its conical sealing surface (138) engages this annular shoulder (136) with a defined pre-stress.

11 Claims, 8 Drawing Sheets

FIG.9

DOSING DEVICE FOR ANALYZING APPARATUS

TECHNICAL FIELD

The invention refers to a dosing device for analyzing apparatus, particularly for liquid chromatography, comprising a) a dosing loop,
b) a change-over valve with a stationary element and an element which is movable between a first and a second position relative to the stationary element, which has a sample inlet and which engages the stationary element with a sealing body, with the change-over valve
   in a first position, connecting the sample inlet to one end of the dosing loop and the other end of the dosing loop to a waste port, and
   in the second position, connecting one end of the dosing loop to a carrier liquid port and the other end of the dosing loop to an analyzing apparatus port,
c) a dosing needle which, by an actuating mechanism, can be introduced with its front end into a sample vessel as well as sealingly into the sample inlet of the change-over valve, and
d) a sample pump which is connected to the rear end of the dosing needle and by which the sample liquid can be aspirated from the sample vessel into the dosing needle when the front end of the dosing needle is in the sample vessel, and by which sample liquid can be pressed out of the dosing needle and can be transferred into the dosing loop when the dosing loop is in the sample inlet of the change-over valve in its first position.

The analyzing apparatus can be a chromatographic separation column for liquid chromatography with a detector which is connected downstream. However, the analyzing apparatus can also be an atomic absorption or atomic emission spectro-photometer, for example, operating with the flow-injection technique. The invention can be applied anywhere where sample liquid shall be introduced into a dosing tube by means of a dosing needle.

BACKGROUND ART

In a prior art dosing device, samples are arranged in sample vessels in a magazine. The sample vessels consist of sample bottles which are closed by a septum. A sample-taking unit is provided on a conveying arm which can be moved according to a program above each of the sample bottles, a rinsing vessel, or the sample inlet. The sample-taking unit comprises a dosing needle which can be introduced into a sample bottle, by penetrating the septum, into the sample inlet or into the rinsing vessel. The change-over valve comprises a stator and a rotor which can be rotated relative to the stator between a first and a second position. The rotor has the sample inlet. The rotor engages the stator with the sealing body. In the first position, the change-over valve connects the sample inlet to one end of a dosing loop and the other end of the dosing loop to a waste port. In the second position, the change-over valve connects one end of the dosing loop to a carrier liquid port and the other end of the dosing loop to an analyzing apparatus port, i.e., a port which leads to a chromatographic separation column, for example. The rear end of the dosing needle communicates through a capillary with a sample pump and a rinsing pump. The rinsing pump has check-valves and aspirates carrier liquid which can be passed by a rinsing process through the dosing needle to the rinsing vessel. Thus, the dosing needle and the capillary are filled up to the tip of the dosing needle by a carrier liquid. Further, the capillary is connected to a sample pump. The sample pump aspirates a volume of a carrier liquid. Thereby, the carrier liquid is sucked back out of the dosing needle so that another medium, air, or sample liquid is aspirated from the tip into the dosing needle.

During operation, the dosing needle is moved above the sample bottle which is located in a predetermined magazine position. First, the dosing needle penetrates only the septum of the sample bottle without dipping into the liquid. Then, the dosing needle is again moved out of the sample bottle. After returning to the starting position, a small volume of air is aspirated by the sample pump. This volume of air serves as a separating layer between the carrier liquid and the sample liquid which shall be aspirated. After a waiting period, the dosing needle penetrates the septum for a second time and now, dips into the sample liquid. The sample pump aspirates a predetermined sample volume and, in addition, a predetermined excess volume into the dosing needle and the dosing capillary. Then, the dosing needle is lifted. The conveying arm moves the dosing needle above the sample inlet of the change-over valve.

In the prior art dosing devices, first, the change-over valve is in its second position in which the dosing loop communicates with a carrier liquid port and an analyzing apparatus port. In this position a part of the excess volume is pressed into the sample inlet in order to rinse the sample inlet with sample liquid. This sample liquid is used for rinsing and runs to a waste vessel. After a waiting period, the change-over valve is rotated to the first position. The sample pump presses the predetermined sample volume into the dosing loop. The displaced volume of carrier liquid is discharged through a capillary. After a further waiting period, the change-over valve is rotated to the second position. The dosed sample volume is conveyed to the analyzing apparatus, here a chromatographic separation column, by a carrier liquid flow which is supplied through the carrier liquid port by a carrier liquid pump. Then, the sample pump pressees the sample liquid and the aspirated air into the sample inlet and through this to a waste port. Subsequently, the rinsing pump carries out a stroke cycle. Hereby, the dosing needle and the sample inlet are rinsed with carrier liquid. This carrier liquid pumped by the rinsing pump also runs through the sample inlet to the waste port. After that, the dosing needle is lifted. The conveying arm moves the dosing needle to a position of rest above the rinsing vessel.

Such arrangements are known from German Patent No. 30 30 3963, which is cognate with U.S. Pat. No. 4,413,534, granted Nov. 8, 1983, and German Patent No. 30 37 014 which is cognate with U.S. Pat. No. 4,393,726, granted Jul. 19, 1983.

Concerning prior art, in the aforementioned German Patent No. 30 30 396 valve of the present type is described which serves as a sample inlet valve and in which a dosing needle is introduced into the rotor up to the engaging surface of the stator, such that it does not penetrate into the stator beyond the engaging surface. For this purpose, the dosing bore in the stator has a smaller diameter than the dosing needle. After supplying the sample to the dosing loop, the rotor is rotated to the second position of the change-over valve. During that time, the dosing needle remains in its position in the rotor. This is necessary so that, by the piston effect of the dosing needle, sample liquid is not re-aspirated from the stator to the rotor. However, during the change-over process, the end of the dosing needle scratches along the engaging surface of the stator. This causes undesired wear and requires the use of particularly hardened engaging surfaces.

According to the aforementioned German Patent No. 30 30 396, an air volume is aspirated into the dosing needle before aspirating the sample liquid. In order to supply the sample to the dosing loop, the dosing needle is introduced with its front end through a bore of the rotor up to the dosing bore of the stator. After supplying the sample to the dosing loop, the air volume is pressed into the dosing loop. Then, before changing over the change-over valve, the dosing needle is withdrawn. Then, through the piston effect during the withdrawl of the dosing needle, only air is re-aspirated while the sample liquid entirely remains within the stator.

In the dosing arrangement according to the aforementioned German Patent No. 30 30 396, the end of the dosing needle is sealingly held with its circumference in the sealing disc of the change-over valve. This is also the case in prior art apparatus which are already in existence.

Thereby, the sealing of the dosing needle in the change-over valve is insufficient. The sealing of the dosing needle undergoes rapid wear. Because of the insufficient sealing, the guideway of the dosing needle has to be rinsed after each dosing.

Further, the volume and the diameter of the dosing loop influence the dosing. The septum of the sample bottle influences the outer moistening of the dosing needle. Finally, when dosing into the sample loop, a counterpressure is required which is generated by a flow resistance in the drain conduit.

German Patent No. 25 07 260 which is cognate with U.S. Pat. No. 4,111,051 granted Sept. 5, 1978, describes a method of supplying a sample in the flameless atomic absorption spectroscopy, in which method a sample liquid is transferred from a sample vessel to a graphite furnace for the electrothermal atomization of the sample. In the method described there, different samples are consecutively aspirated from sample vessels by means of a dosing tube. Subsequently, the dosing tube is moved to the graphite furnace, and the aspirated sample is supplied to this graphite furnace. Between each of the aspirating and supplying cycles of different samples, a rinsing process takes place. For this rinsing process, rinsing liquid is passed from the end remote from the aspirating end into the dosing tube and is supplied through this dosing tube to a rinsing vessel. After the rinsing process, the interior of the dosing tube is filled with rinsing liquid. After the rinsing process and before aspirating the sample, a small volume of air is aspirated into the dosing tube. After supplying the sample to the graphite tube, this air volume, together with a sample volume, is again pressed out of the dosing tube. In the prior art arrangement, an air and a sample pump, respectively, are provided in order to aspirate the air volume and the sample volume. Further, a rinsing liquid pump which aspirates rinsing liquid from a rinsing liquid vessel and pumps only in one direction communicates through check valves with the dosing tube. German Patent No. 36 03 632 shows a particular construction of such a rinsing liquid pump.

German Patent No. 31 25 632 which is cognate with U.S. Pat. No. 4,461,185, granted Jul. 24, 1984, shows an injection cannula for taking a liquid sample from sample vessels which are closed by a self-sealing membrane. This injection cannula consists of a capillary tube which is conically tapered at its ends, as well as at its interior.

German Published Patent Application No. 37 20 289 describes a method of electrothermal atomization of samples in which the sample is pressed by a carrier liquid through a dosing tube through a heated capillary, with the sample precipitating at the walls of a preheated graphite furnace. Then, the thus-precipitated sample is detected by the atomic absorption spectroscopy.

DISCLOSURE OF THE INVENTION

It is the object of the invention to design a dosing device of the above-mentioned type so that a secure sealing between the dosing needle and the sample inlet is guaranteed.

According to the invention, this object is achieved in that e) the dosing needle forms at its front end a sealing surface which is tapered at the end, and f) the sample inlet comprises a sample inlet passage in the sealing body of the change-over valve, with this sample inlet passage having a straight first section into which the front end of the dosing needle can be introduced, and a second section communicating therewith, which has a smaller cross-section and opens into the control surface between the sealing body and the stationary element, and an annular shoulder between the first and the second sections, which is substantially complementary to the sealing surface of the dosing needle.

Thus, a seal caused by force results between the sealing surface of the dosing needle and the annular shoulder. Thereby, in practice, no sample liquid can get into the needle guideway. Thus, the danger of a carry-over is substantially reduced. There is no wear of the seal. The sealing surface of the stator is also not affected by the dosing needle.

A needle guideway with a guiding channel for the dosing needle can be provided in the movable element of the change-over valve, with the guiding passage widening in a funnel-shaped fashion at the outer end. This facilitates the introduction of the dosing needle into the sample inlet.

The dosing needle can be arranged on a rack body which is movably guided in a carrier and which is provided with a longitudinal rack. The rack meshes with a pinion which can be driven by a servomotor. The rack body is preferably sleeve-shaped. A needle carrier is guided into the sleeve-shaped rack body. The dosing needle extends longitudinally through the needle carrier. The dosing needle is held in the needle carrier so that it projects out of the first end of the needle carrier. At its first end, the needle carrier engages a stop. A preloaded spring which is supported by the rack carrier engages the opposite second end.

In this way, first of all, the needle has a defined position relative to the rack body which is determined by the stop. When the dosing needle engages the annular shoulder in the sealing body, the spring is compressed upon further movement of the rack body. This results in a defined pressure force of the sealing surface of the dosing needle to the annular shoulder. In practice, first of all, the dosing needle is lowered by the step motor for a defined number of steps into the sample inlet. Thereby, the dosing needle does not yet contact the annular shoulder. After that, there is a further lowering of ten steps, for example. After each such lowering, the power supply of the step motor is switched off. When the dosing needle contacts the annular shoulder, the step motor, after the switching-off of the power supply, moves backwards because of the mechanical pressure and then, comes to a stop. After that, the dosing needle is moved back to the starting position. The steps which are necessary for that are counted. Then, with each dosing, the dosing needle is moved forward into the sample inlet by the thus-measured step number plus a fixed step number of 40, for example. Then, it is guaranteed that the dosing needle engages the annular shoulder with a defined sealing force.

At the carrier a bottle holding-down device can be movably guided parallel to the rack body. The bottle holding-down device is loaded by a spring in the pushing direction of the rack body. A dog is provided at the rack body which dog, under the influence of the spring, engages the bottle holding-down device. The bottle holding-down device, together with the rack body and the dosing needle, moves downwards until the bottle holding-down device engages a sample bottle which serves as sample vessel. When the dosing needle with the needle carrier moves further downwards into the sample bottle, the bottle holding-down device lifts up from the dog. When moving the dosing needle backwards, the bottle holding-down device prevents the dosing needle from taking the sample bottle along until the dosing needle has left the sample bottle. Then, the dog again takes the bottle holding-down device along.

The bottle holding-down device is provided with an actuating member which initiates a changing-over process when the bottle holding-down device is taken along with the rack body further than to the level of the common sample vessels.

The movable element of the change-over valve can be a rotor which is rotatable relative to the stationary element (stator). The first and the second positions of the rotor are determined by two stops. The changing-over is made by a rotary drive the axis of which is parallel to the axis of the rotor. The rotary drive is connected to the rotor by a linkage. The rotary drive can be switched off when reaching one of the stops. Spring members are provided in the linkage. Advantageously, the linkage has a pivoting lever which is connected to the rotary drive and which has a link block at its end. Further, the linkage has a pivoting lever which is connected to the rotor. The first and the second pivoting levers are connected by a bar. The link block is movably guided on the bar and is held between two counter-acting, loaded springs.

In this way, it is not required to provide a sliding clutch between the drive and the change-over valve as is usual in dosing devices of this type. The linkage construction is substantially less expensive. Moreover, the precision of the adjustment of the change-over valve is increased.

In a further embodiment of the invention, the sample pump, which is the only pump, can selectively be connected through a change-over valve to either a vessel with carrier liquid or to the dosing needle. In this way, one pump is saved. Problems occurring with rinsing pumps (comp. the aforementioned German Patent No. 36 03632) are avoided.

An embodiment of the invention will now be described in further detail with reference to the accompanying drawings.

PREFERRED EMBODIMENT OF THE INVENTION

Figure 1:
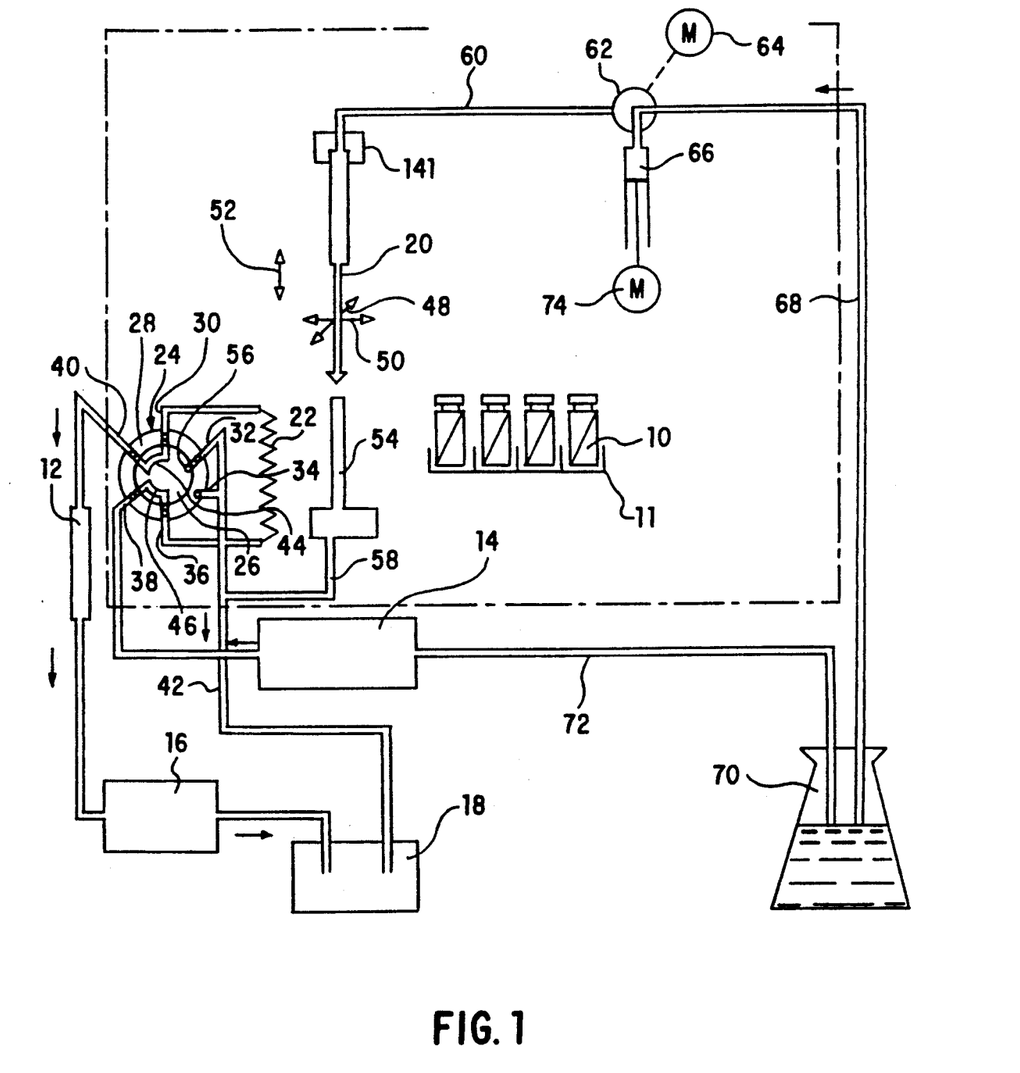
FIG. 1 shows schematically a dosing device for liquid chromatography with a switch-over valve in a position in which a sample pump aspirates carrier liquid.

The dosing device according to FIG. 1 serves for guiding sample liquid from a sample vessel 10 to the inlet of a separating column 12 for liquid chromatography. Then, the sample liquid is conveyed by a carrier liquid which is pumped by a pump 14 through the separating column 12. The substances emerging from the exit of the separating column are detected by a detector 16 in the known way. The exit of the detector 16 is connected to a waste vessel 18. The sample vessels 10 are sample bottles which are closed by a septum. The sample bottles are arranged in a magazine 11 in a usual way. A dosing needle 20, a sample or dosing loop 22, and a change-over valve 24 are provided in order to transfer a defined amount of sample liquid to the inlet of the separating column 12.

The change-over valve 24 comprises a rotor 26 and a stator 28. The stator 28 has six ports 30, 32, 34, 36, 38 and 40. The port 30 is connected to a first end of the dosing loop 22. The ports 32 and 34 are connected in parallel through a conduit 42 to the waste vessel 18. The port 36 is connected to the second end of the dosing loop 22. The port 38 is connected to the outlet side of the pump 14. The port 40 is connected to the inlet of the separating column 12. Each of the ports of the stator 28 is set off at an angle of 60°. The rotor 26 has two connecting passages 44 and 46. The two connecting passages are spaced by 60° from each other and each extend over an angle of 60°. Thus, communication between two adjacent ports of the stator 28 can be achieved by the connecting passages 44 and 46.

As indicated by the double arrows 48 and 50, the dosing needle 20 can be moved with a carrier in two coordinates. Further, it can be vertically lowered and lifted relative to the carrier, as indicated by the double arrow 52 by means of an actuating mechanism 141 as described further hereinbelow with reference to FIG. 7.

With the carrier, the dosing needle 20 is selectively movable above a programmed magazine position and thus above either a sample vessel 10, a rinsing vessel 54, or a sample inlet 56 which is provided on the rotor 26 of the change-over valve 24. The rinsing vessel 54 is designed as an overflow vessel and is connected through a conduit 58 to a conduit 42 leading to the waste vessel 18.

The dosing needle 20 communicates through a capillary 60 with the switch-over valve 62. The switch-over valve 62 can be switched by a servomotor 64 between two switching positions. In the first switching position illustrated in FIG. 1, the switch-over valve 62 connects a sample pump 66 to a conduit 68 which is guided to a carrier liquid vessel 70. The carrier liquid vessel 70 is also connected through a conduit 72 to the inlet of the pump 14. The sample pump 66 can be driven by a motor 74. The drive is made such that the piston of the sample pump 66 makes a well-defined stroke. In a second switching position, which is illustrated in FIG. 2, communication is provided through the switch-over valve 62 between the sample pump 66 and the capillary 60 and thus the dosing needle 20.

Figure 2:
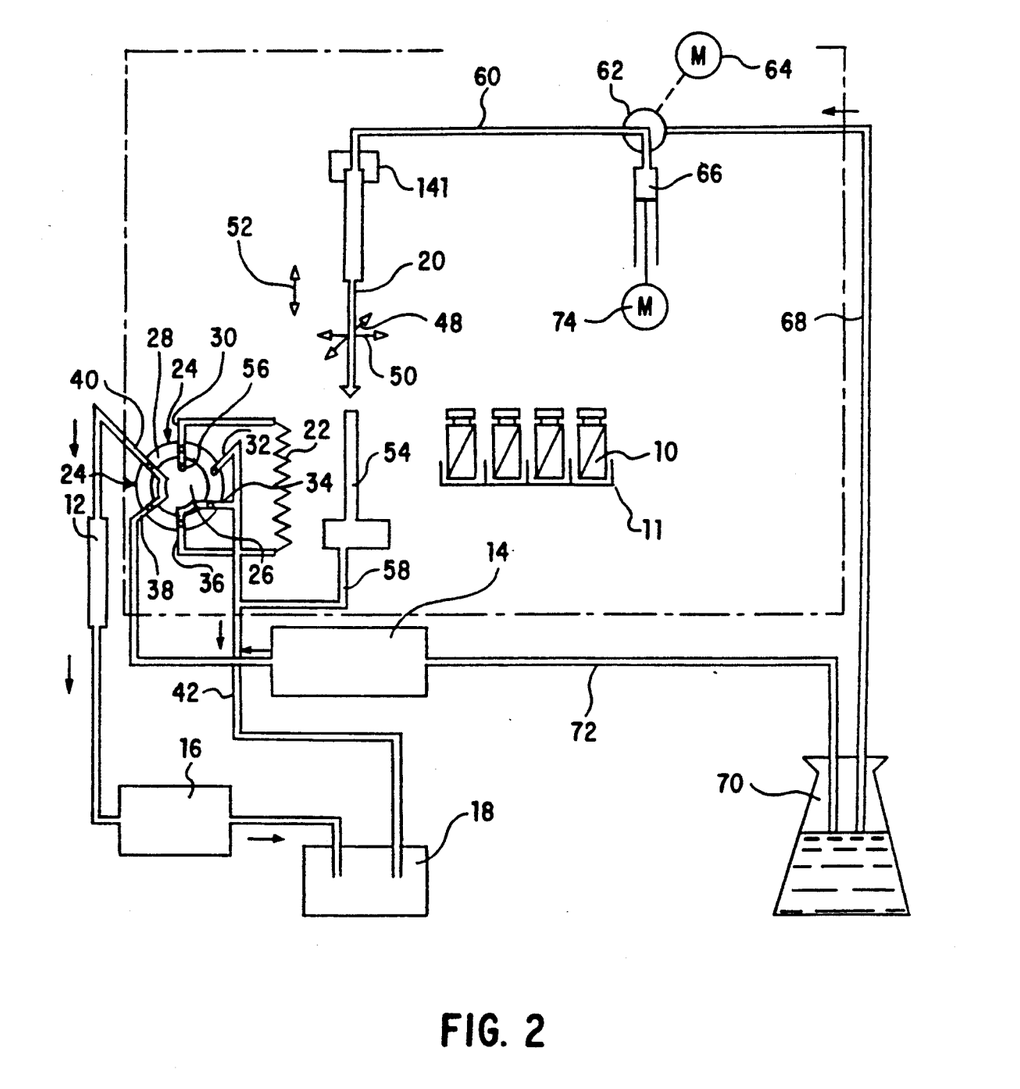
FIG. 2 shows the dosing device of FIG. 1 with the switch-over valve in a second position in which the sample pump is connected to a dosing needle.

In FIG. 2, the change-over valve 24 is illustrated in its first position. In FIG. 1, the change-over valve 24 is in its second position. The two positions of the change-over valve 24 are once again illustrated in an enlarged fashion in FIGS. 3 and 4.

Figure 3:
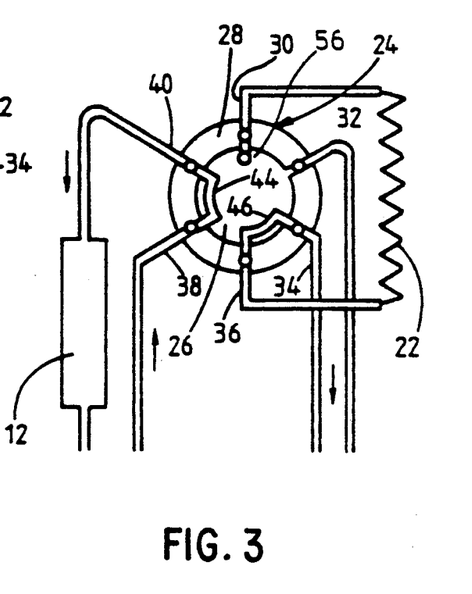
FIG. 3 shows a change-over valve in the dosing device of FIG. 1 in a first position.

In the first position of the change-over valve 24 illustrated in FIG. 3 communication between the ports 38 and 40 is provided through the connecting passage 44. Then, the carrier liquid pumped by the pump 14 flows through the port 38, the passage 44, and the port 40 to the inlet of the separating column 12. In the first position of the change-over valve 24, the sample inlet 56 communicates with the port 30 and thus with the first end of the dosing loop 22. The second end of the dosing loop 22 communicates through the port 36, the connecting passage 46, and the port 34 with the waste vessel 18.

In the second position (FIG. 4) of the change-over valve 24, the port 38 communicates through the connecting passage 46 with the port 36 and the port 30 through the connecting passage 44 with the port 40. As can be seen from FIG. 4, in this position, the dosing loop 22 is connected in series to the separating column 12. A flow of carrier liquid from the pump 14 flows through the port 38, the connecting passage 46, and the port 36 to the dosing loop 22 and from the second end of the dosing loop 22 through the port 30, the connecting passage 44, and the port 40 to the inlet of the separating column 12.

The described arrangement operates as follows:

In the first position of the switch-over valve 62 illustrated in FIG. 1, carrier liquid is aspirated by the sample pump 66 from the carrier liquid vessel 70 through the conduit 68. After switching over the switch-over valve 62 (FIG. 2), this carrier liquid which serves here as a washing liquid, is supplied through the capillary 60 and the dosing needle 20 into the rinsing vessel 54. Now, the dosing needle 20 is filled up to its tip or front end 137 with carrier liquid. Then, a small volume of air is aspirated through the sample pump 66 which air volume shall separate the sample liquid from the carrier liquid in the dosing needle 20. The sample pump 66 aspirates pure carrier liquid and the carrier liquid, thereby aspirated through the switch-over valve 62 from the dosing needle 20 and the capillary 60, effects an aspiration into the dosing needle 20. Then, the dosing needle 20 is moved with its actuating mechanism 141 above a sample vessel 10, i.e. a sample bottle. The dosing needle 20 is lowered and penetrates the septum of the sample bottle. The sample pump 66 aspirates through the switch-over valve 62 a further volume of carrier liquid from the dosing needle 20 whereby sample liquid is aspirated from the sample bottle into the dosing needle 20. Then, the dosing needle 20 is again lifted and is withdrawn from the sample bottle.

As the next step, the dosing needle 20 is moved above the sample inlet 56. In FIG. 2, the change-over valve 24 is in its first position. The sample inlet 56 of the rotor 26 is connected to the port 30 of the stator. The port 30 is connected to the first end of the dosing loop 22. The second end of the dosing loop 22 communicates through the port 36, the connecting passage 46, and the port 34 with the waste vessel 18. Now, the sample pump 66 makes a discharge stroke and thereby presses sample liquid into the sample 56 inlet and into the sample loop 22. The carrier liquid which was still present in the sample loop 22 is displaced and flows to the waste vessel 18.

Figure 4:
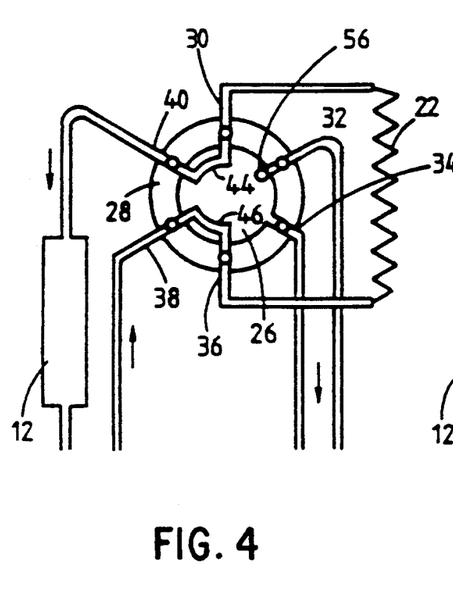
FIG. 4 shows the change-over valve in a second position.

Now, the change-over valve 24 is switched to the second position which is illustrated in FIG. 4. With this change-over, the dosing needle 20 remains in the sample inlet 56. The dosing needle 20 accompanies the rotor 26 in its rotational movement. In the second position of the change-over valve 24, the sample liquid which is introduced into the sample loop 22 is conveyed by the carrier liquid flow into and through the separating column.

During this process, the sample pump 66 can press the remaining sample liquid out of the dosing needle 20 and can subsequently press carrier liquid into the sample inlet 56 in order to rinse the sample inlet 56, with these liquids then flowing off through the port 32 of the change-over valve 24 to the waste vessel 18. Then, the dosing needle 20 is withdrawn from the sample inlet 56 and is moved above the rinsing vessel 54. There, if required, an additional rinsing can be provided. Then, the switch-over valve 62 again switches to the first position illustrated in FIG. 1, in which the sample pump 66 can aspirate carrier liquid from the carrier liquid vessel 70.

Figure 5:
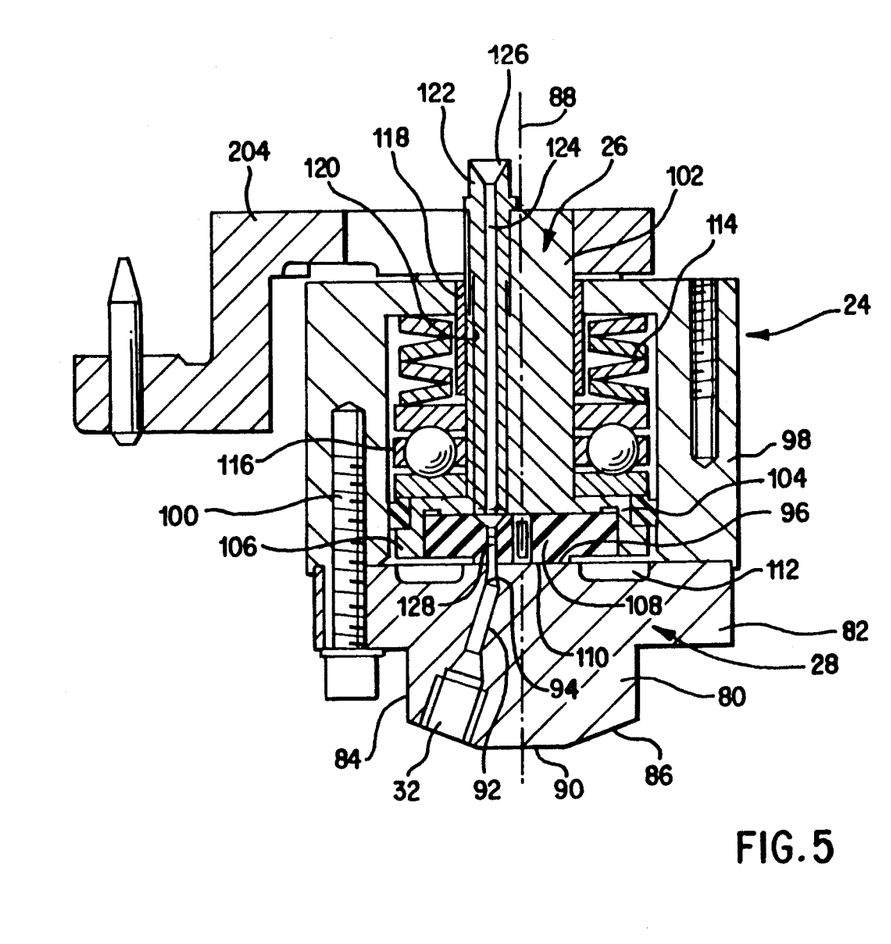
FIG. 5 shows a longitudinal section taken through the change-over valve.
Figure 6:
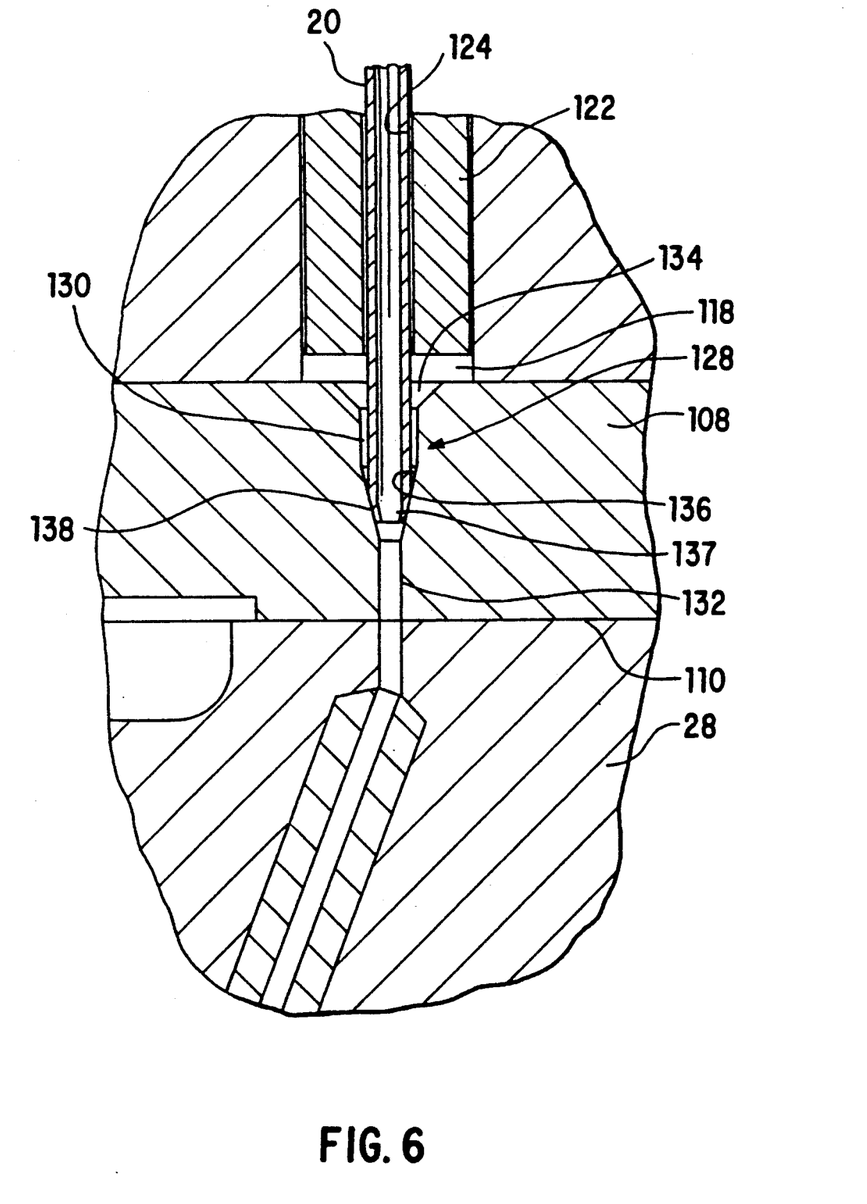
FIG. 6 shows a detail of the change-over valve of FIG. 5 with the dosing needle introduced.

The construction of the change-over valve 24 is illustrated in FIGS. 5 and 6.

The stator 28 of the change-over valve 24 forms a housing which surrounds the rotor 26. The stator 28 has a head portion 80 in which the ports 30 to 40 are formed. In FIG. 5, only the port 32 is illustrated. The head portion 80 is formed by a disc 82 with a central boss 84. The end face of the central boss 84 forms a flat-conical annular surface 86 which surrounds a plane surface 90 which extends perpendicular to the axis 88 of the stator 28. The ports, e.g. port 32, are provided in the flat-conical annular surface 86. Then, the ports change into passages 92 which extend transversely inwardly and which in turn change into narrow, axial passages 94 which end in a circular array around the axis 88 in a control surface 96 on the side of the stator 28.

A pot-shaped housing element 98 is connected to the head portion 82 by screws 100. The housing element 98 surrounds the rotor 26. The rotor 26 comprises a shaft 102. The shaft ends in a plate 104 with a rim 106. A disc-shaped sealing body 108 is held in the plate 104 with the rim 106. The sealing body 108 has in its central area a projecting control surface 110 which engages the control surface 96 of the stator 28. An annular groove 112 is provided in the head portion 80 around the control surface 96. Correspondingly, the rim 106 and the sealing body 108 are set back around the control surface 110. The rotor 26 is pressed by a disc spring 114, which is supported by the "bottom" of the housing element 98, through a thrust bearing 116 against the head portion 82 of the stator 28.

In a bushing 118, the shaft 102 of the rotor 26 is rotatably mounted in the stator 28 and is guided out of the pot-shaped housing element 98 through the "bottom". The diameter of the shaft 102 approximately corresponds to that of the control surface 110.

The shaft 102 is provided with an eccentric bore 120 into which a needle guideway 122 is screwed. The needle guideway 122 has a longitudinal bore 124 which forms a funnel-shaped enlargement 126 at its outer end, i.e. at its upper end in FIG. 5. The longitudinal bore 124 is aligned with a sample inlet passage 128 in the sealing body 108.

The sample inlet passage 128 can be better recognized in FIG. 6. The sample inlet passage 128 comprises a straight first section 130 into which the tip or front end 137 of the dosing needle 20 can be inserted, as illustrated in FIG. 6. The first section 130 communicates with a second section 132 having a smaller diameter. The second section 132 is aligned with the first section 130 and ends in the control surface 110 of the sealing body 108. The first section 130 opens on the side of the eccentric bore 120 in a funnel-shaped enlargement 134. A conical annular shoulder 136 is integral with the first section 130 and the second section 132 of the sample inlet passage 128 and is arranged inbetween. At its tip or front end 137 (at the bottom of FIG. 6), the dosing needle 20 forms a conical sealing surface 138 which is tapered at its end. The sealing surface 138 sealingly engages the conical annular shoulder 136.

Figure 7:
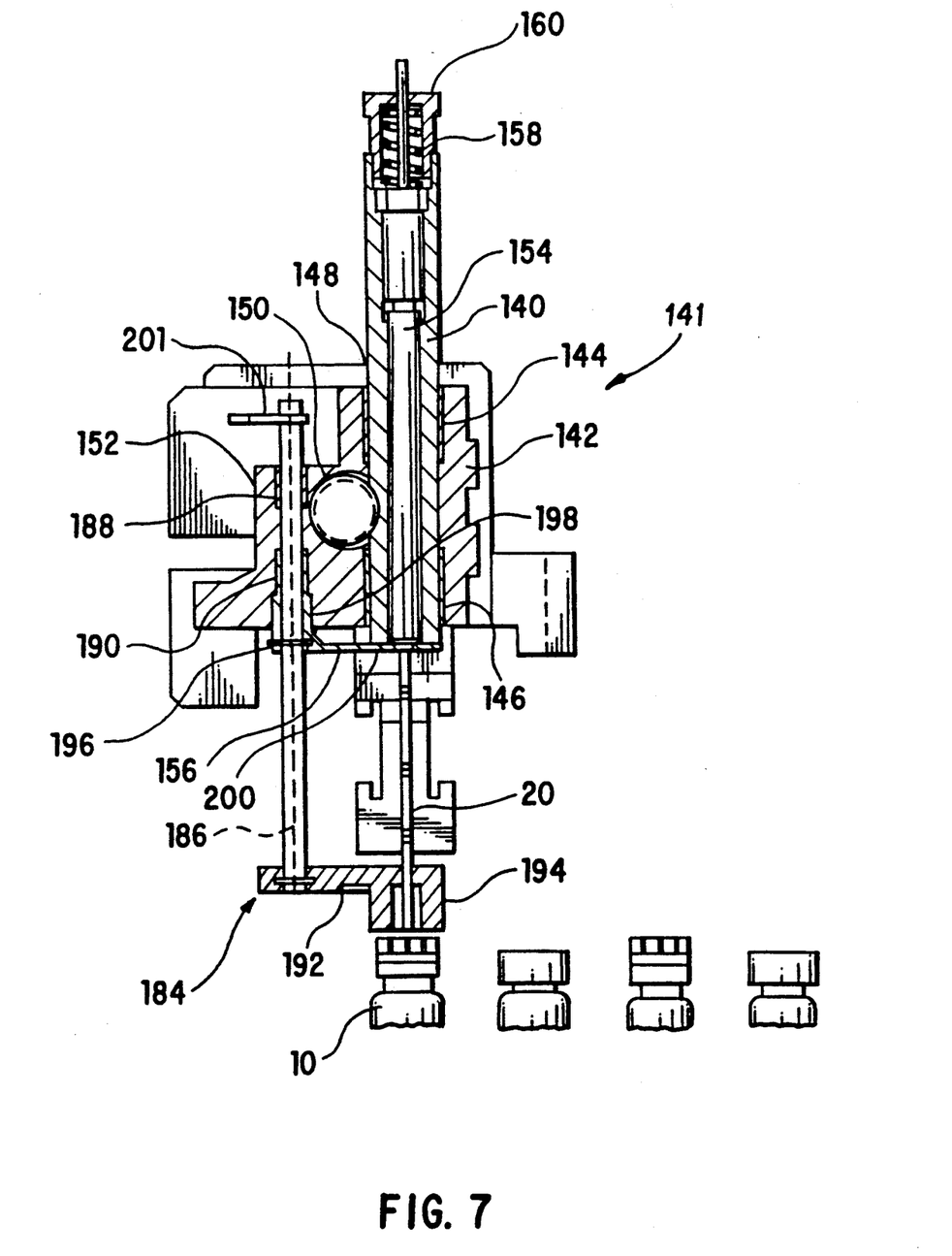
FIG. 7 shows the actuating mechanism for the dosing needle.

FIG. 7 shows the actuating mechanism 141 for moving the dosing needle up and down. The rack body 140 is vertically movably guided in a carrier 142 in bushings 144 and 146. The rack body 140 is designed in a sleeve form. At one end, the rack body 140 is integral with a rack 148. The rack 148 meshes with a pinion 150 which is driven by a step motor 152. By the step motor 152 and the pinion 150, the rack 148 and the rack body 140 are, under controlled conditions, vertically movable relative to the carrier 142. The step motor 152 is controlled by a (not illustrated) control unit in a known manner.

A needle carrier 154 is movably guided in the sleeve-shaped rack body 140. A dosing needle 20 is arranged in the needle carrier 154. The dosing needle 20 longitudinally extends through the needle carrier 154. The dosing needle 20 is held by the needle carrier 154 such that it projects from the lower end of the needle carrier 154. A stop 156 is provided at the lower end of the rack body 140. A helical spring 158 engages the upper end of the needle carrier 154. The helical spring 158 is pre-loaded and is supported by a cap 160 which is screwed into the upper end of the sleeve-shaped rack body 140. Therefore, upon overcoming the pre-load of the spring 158, the dosing needle 20 can be moved to the top relative to the rack body, 140 with the needle carrier 154 lifting up from the stop 156.

Figure 8:
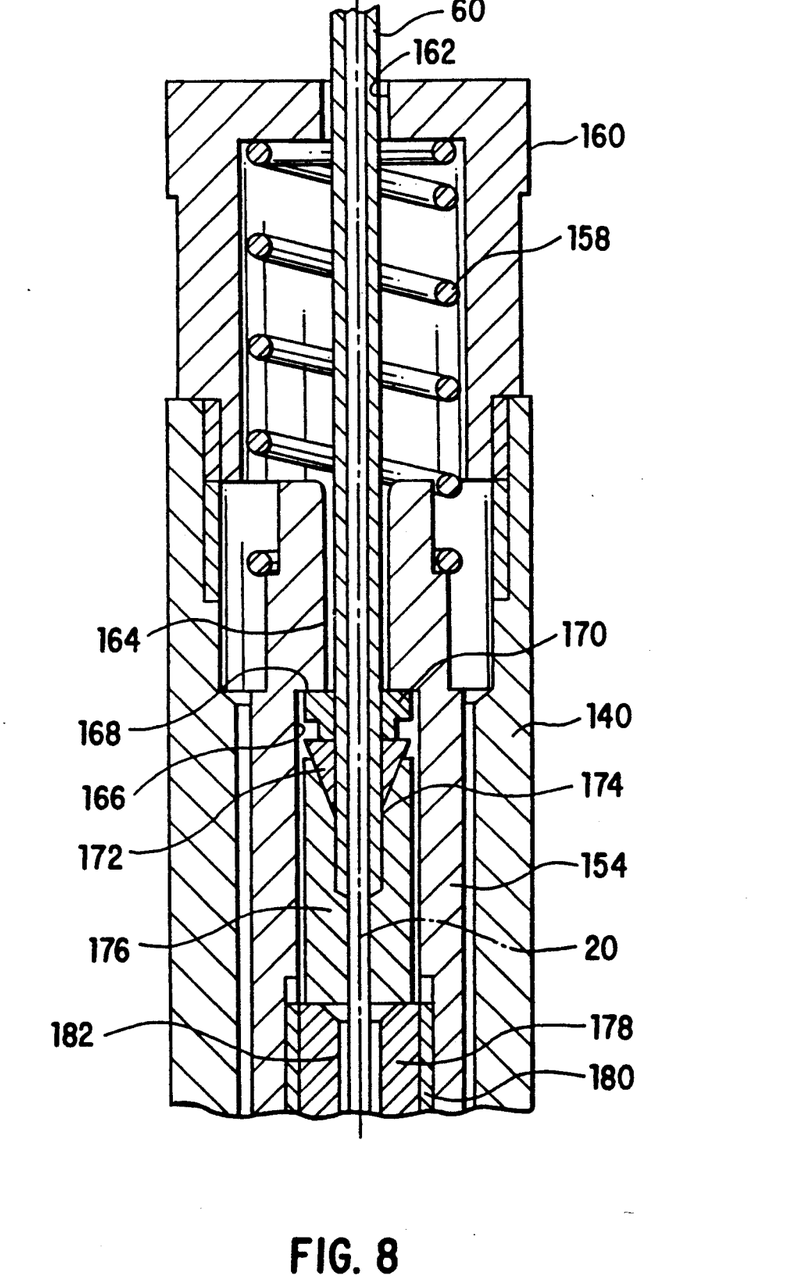
FIG. 8 shows a detail of FIG. 7.

In FIG. 8, the upper portion of the rack body 140 with the cap 160 and the needle carrier 154 is illustrated on an enlarged scale. The capillary 60 is guided through an aperture 162 of the cap 160 and is slipped onto the upper end of the dosing needle 20. The capillary 60 extends into a longitudinal bore 164 of the needle carrier 154. The longitudinal bore 164 changes to a longitudinal bore 166 of a larger diameter. An annular shoulder 168 is formed between the longitudinal bores 164 and 166. An annular thrust member 170 engages the annular shoulder 168. The thrust member 170 surrounds the capillary 60 and the dosing needle 20. A conical clamp element 172 which also surrounds the capillary 60 and the dosing needle 20 engages the thrust element 170 at its lower side. The conical clamp body 172 projects into a substantially complementary, funnel-shaped cutout 174 in the end face of a thrust element 176. The thrust element 176 engages a threaded element 178 which is guided in a threaded bore 180. The threaded bore 180 is annexed to the longitudinal bore 166. The threaded element 178 has a longitudinal bore 182 through which the dosing needle 20 is guided. By tightening the threaded element 178 against the thrust element 176 and through the clamp element 172 and the thrust element 170 against the annular shoulder 168, the clamp element 172 is radially compressed whereby the capillary 60 is securely clamped to the dosing needle 20.

A bottle holding-down device 184 is vertically movably guided on the carrier 142. The bottle holding down device 184 comprises a rod 186 which is guided into bushings 188 and 190 in a bore of the carrier 142. An arm 192 is provided at the lower end of the rod 186 which arm can be attached with a head 194 to a sample bottle serving as a sample vessel 10.

The rod 186 is provided with a ring 196. A helical spring 198 engages the ring 196. The helical spring 198 is provided in an enlargement of the guiding bore for the rod 186 and is supported by the carrier 142. The spring tends to press the rod 186 and thus the arm 192 and the head 194 to the bottom. However, the ring 196 engages a dog 200 which is connected to the rack body 140. Thereby, for the present, the bottle holding-down device 184 is held in a fixed position relative to the rack body 140.

When the rack body 140 together with the dosing needle 20 moves downwards, the bottle holding-down device 184 follows until the head 194 engages the sample bottle. As can be seen from FIG. 7, the lower tip of the dosing needle 20 approximately lies in the plane of the lower end face of the head 194. When the rack body 140 moves further down, the dosing needle 20 penetrates through the septum of the sample bottle into the sample bottle. The bottle holding-down device 184 cannot follow this movement. The dog 200 detaches from the ring 196. When, after aspirating the sample, the rack body 140 with the dosing needle 20 again moves upwards, with the dosing needle 20 being pulled out of the septum, the bottle holding-down device 184 prevents the sample bottle from also being lifted, through the friction between the dosing needle 20 and the septum and finally falling back onto the magazine 11. When the sample bottle falls back there is the danger that sample liquid is dispersed. When the dosing needle 20 is finally completely pulled out of the septum of the sample bottle, as is indicated in FIG. 7, the dog 200 again engages the ring 196 and again takes the bottle holding down device 184 along to the top.

The upper end of the rod 186 is provided with an arm 201. This arm 201 cooperates with a (not illustrated) micro-switch as "bottle sensor". When there is a magazine position without any sample bottle, the bottle holding down device 184 is not held back from a sample bottle but moves further down with the dosing needle 20 beyond the position illustrated in FIG. 7. Then, the arm 201 actuates the micro-switch and signals that there is no sample bottle in this location.

Figure 9:
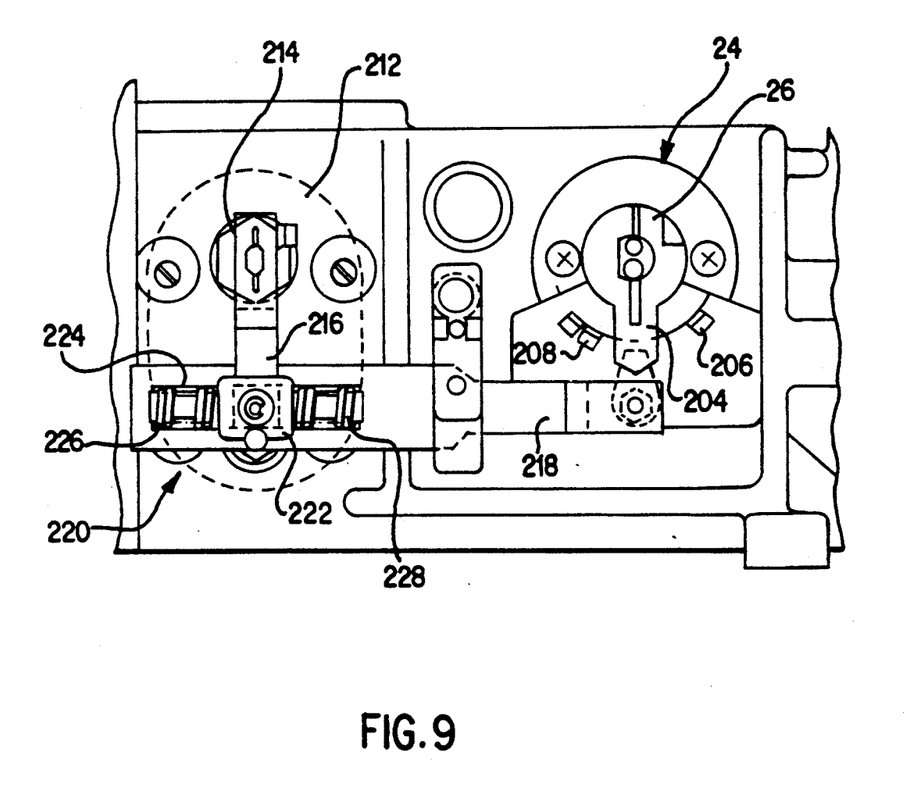
FIG. 9 shows the drive unit for the change-over valve in the dosing device of FIG. 1.

FIG. 9 is a plan view and shows the change-over valve 24 and the associated drive unit 212. The rotor 26 of the change-over valve 24 is provided with a pivoting lever 204. As can be seen from FIG. 5, the pivoting lever 204 is downwardly bent at an angle in a z-shaped fashion. The central portion 202 extending parallel to the stater axis 88 moves along the peripheral surface of the change-over valve 24. This peripheral surface is provided with two stops 206 and 208. These stops 206 and 208 determine the first and the second positions of the change-over valve 24. Numeral 212 designates a rotary drive unit in the form of a servomotor. The axis 214 of the servomotor 212 is provided with a pivoting lever 216. The pivoting lever 216 is connected with the pivoting lever 204 through a rod 218. The pivoting levers 204 and 216 and the rod 218 form a linkage 220. The end of the pivoting lever 216 is provided with a block 222. The block 222 is movably guided into a guideway 224 in the longitudinal direction of the rod 218. However, the block 222 is held between two helical springs 226 and 228.

The change-over valve 24 can be switched between the first and second positions by the servomotor 212. The servomotor 212 moves the pivoting lever 204 until it engages e.g. the stop 208. The stop 208 simultaneously works as the end switch for the servomotor 212. By a certain after-running of the servomotor 212, the spring 228 is compressed a little bit more. After the servomotor 212 comes to a stop, the spring 228 partially relaxes. The remaining stress of the spring 228 in a bounce-free fashion presses the pivoting lever 204 through the bar 218 against the stop 208.

In the same way the switching to the second position is accomplished in which the pivoting lever 204 engages the stop 206. The described way of changing-over ensures a well-defined position of the rotor 26 in the two positions of the change-over valve 24.

The change-over valve 24 and the dosing needle 20 cooperate as follows:

The servomotor 212 moves the rotor 26 of the change-over valve 24 to the first position illustrated in FIG. 3. Thereby, the pivoting lever 204 engages the stop 208. By prior art means which are not further illustrated, the dosing needle 20 is moved with the carrier 142 above the sample inlet 56 which, in the first position of the change-over valve 24, is in the plane of the port 30. The sample inlet 56 comprises the needle guideway 122 and the sample inlet passage 128. Then, the sample inlet passage 128 communicates with the port 30 in the manner as illustrated in FIG. 5 for the port 32. The step motor 152 moves the rack body 140 with the dosing needle 20 downwards by means of the pinion 150 and the rack 148. Thereby, the dosing needle 20 is introduced by the needle guideway 122 into the sample inlet passage 128. Then, in stages of ten steps each, the step motor 152 advances the dosing needle 20. After ten steps each, the power supply of the step motor 152 is disconnected for a short time. When the dosing needle 20 engages the conical annular shoulder 136, the spring 158 is slightly compressed with further steps of the step motor 152. After disconnecting the power supply of the step motor 152, the rack body 140 is pressed back by the force of the spring 158 and the step motor 152 is slightly rotated back. This process is detected and indicates that the dosing needle 20 engages the annular shoulder 136.

With the subsequent withdrawl of the dosing needle 20 from the sample inlet 56 and the movement to its elevated original position, the necessary steps of the step motor 152 are counted. With the subsequent reintroduction of the dosing needle 20 into the sample inlet 56 for the following dosing processes, the dosing needle 20 is advanced by the step motor 152 by the thus determined number of steps and, in addition, by another forty steps. These additional forty steps effect a stress of the spring 158 and guarantee that the conical sealing surface 138 of the dosing needle 20 engages the conical annular shoulder 136 of the sealing body 108 with a defined sealing power. In this way, frictional sealing between the dosing needle 20 and the sealing body 108 is achieved. The sealing is virtually resistant to wear. The pre-stress of the spring 158 alway guarantees a sufficient contact force.

We claim:

1. Dosing device for analyzing apparatus, comprising:

a dosing loop (22) having a first end and a second end;

a change-over valve (24) connected to said dosing loop (22) and containing a stationary member (28) and a movable member (26) which is movable between a first and a second position relative to the stationary member (28);

said movable member (26) of said change-over valve (24) containing a sample inlet (56) and a sealing body (108) interposed between said movable member and said stationary member;

said change-over valve (24) assuming a first position in which the sample inlet (56) is connected to the first end of the dosing loop (22) and the second end of the dosing loop (22) is connected to a waste port (42) of the stationary member (28);

said change-over valve (24) assuming a second position in which the second end of the dosing loop (22) is connected to a carrier liquid port of the stationary member and the first end of the dosing loop (22) is connected to an analyzing apparatus port of the stationary member;

a dosing needle (20) having a front end and a rear end;

an actuating mechanism (141) coupled to said dosing needle (20) for selectively introducing the front end of the dosing needle into either one of a sample vessel (10) or the sample inlet (56) of the change-over valve (24);

a sample pump (66) connected to the rear end of the dosing needle (20) for aspirating sample liquid from the sample vessel (10) into the dosing needle (20) when the front end of the dosing needle (20) is placed in the sample vessel (10);

wherein said sample pump (66) transfers aspirated sample liquid from the dosing needle (20) into the dosing loop (22) when the first end of the dosing loop (22) is connected to the sample inlet (56) of the change-over valve (24) in the first position of the change-over valve;

the dosing needle (20) having formed at its front end (137) a tapered sealing surface (138);

the sample inlet (56) of said movable member (26) of the change-over valve (24) comprising a sample inlet passage (128) extending through the sealing body (108) of the change-over valve (24);

said sample inlet passage (128) having a straight first section (130) for receiving the front end (137) of the dosing needle (20) in a spaced relationship;

said sample inlet passage having a second section (132) having a smaller cross-section than said straight first section;

said sealing body (108) interposed between said movable member (26) and said stationary member (28) of said change-over valve (24), defining a control surface (110) which engages said stationary member and into which opens said second section (130) of said sample inlet passage (128);

an annular shoulder (136) defined between the straight first section (130) and the second section (132) of said sample inlet passage (128) within said sealing body (108) of said movable member (26) of the change-over valve (24); and said annular shoulder (136) having a tapered configuration substantially complementary to said tapered sealing surface (138) formed at the front end (137) of said dosing needle (20) for sealing engagement with said front end (137) of said dosing needle (20).

2. Dosing device as set forth in claim 1, wherein said movable member (26) of said change-over valve (24) is provided with a needle guideway (122) containing a guiding passage (124) for the dosing needle (20), said guiding passage (124) having a funnel-shaped external end (126).

3. Dosing device as set forth in claim 1, wherein:

said actuating mechanism (141) comprises a rack body and a carrier (142) for said rack body (140) having the form of a sleeve;

said dosing needle (20) extending through said rack body (140) and being mounted with a portion between its ends at a needle carrier (154) inserted into the rack body;

said rack body (140) being movably guided in said carrier (142) and provided with a longitudinal rack (148);

a servomotor (152);

a pinion (152) drivingly connected to said servomotor (152) for displacing said rack body (140) and thereby said dosing needle (20) relative to said carrier (142); and the longitudinal rack (148) of said rack body (140) meshing with said pinion (150).

4. Dosing device as set forth in claim 3, wherein the servomotor (152) is a step motor.

5. Dosing device as set forth in claim 3, wherein:

said needle carrier (154) being guided in the rack body (140);

said needle carrier (154) has a first end and a second end;

said dosing needle (20) extending longitudinally through said needle carrier (154) and projecting from said first end of said needle carrier;

said rack body (140) comprising a stop (156) for engaging said first end of said needle carrier (154) and limiting movement of said needle carrier (154) in said rack body (140) in a predetermined movement direction; and a preloaded spring (158) being supported at said rack body (140) and biassing said second end of said needle carrier (154) in said predetermined movement direction.

6. Dosing device as set forth in claim 3, wherein:

said actuating mechanism (141) comprises a bottle holding-down device (184) for holding down the sample vessel (10) during the time said dosing needle (20) is being withdrawn from said sample vessel (10) under the action of said actuating mechanism (141) after sample liquid has been aspirated into said dosing needle (20);

said bottle holding-down device (184) being guided at the carrier (142) for movement parallel to the rack body (140);

a spring (198) mounted at said carrier (142) and acting upon said bottle holding-down device (184) in order to bias the bottle holding-down device in a direction towards the sample vessel (10) from which sample liquid is taken up into the dosing needle (20); and a dog (200) being provided at the rack body (140) and coupled to the bottle holding-down devive (184) under the force of the spring (198).

7. Dosing device as set forth in claim 6, wherein:

a sensor member (201) is provided at the bottle holding-down device (184); and said actuating member (201) being movable conjointly with said bottle holding-down device (184) for sensing excessive movement of the bottle holding-down device in the event of absence of a sample vessel (10).

8. Dosing device as set forth in claim 1, wherein:

the movable member (26) of the change-over valve (24) is a rotor which is rotatable relative to the stationary member (28) about an axis of the stationary member of the change-over valve (24);

said change-over valve (24) comprising a first stop (206) and a second stop (208) for limiting rotational movement of said rotor and respectively defining said first position and said second position of said change-over valve (24);

a rotary drive unit (212) for rotatably moving said rotor between said first stop and said second stop;

a linkage (220) drivingly connecting said rotary drive unit (212) and said rotor;

said rotary drive unit (212) being switched off when either one of the first and second stops (206, 208) is reached; and spring members (226, 228) being provided in the linkage (220).

9. Dosing device as set forth in claim 8, wherein:

the linkage (220) comprises a first pivoting lever (216) having two ends one of which is connected to the rotary drive unit (212) and an other one of which is provided with a link block (222);

the linkage (220) further comprises a second pivoting lever (204) which is connected to the rotor;

a bar (218) interconnecting the first and second pivoting levers (216, 204); and the link block (222) being movably guided at the bar (218) and held between said spring members (226, 228) constituting two counteracting preloaded springs.

10. Dosing device as set forth in claim 1, further comprising:

a switch-over valve (62) connected to said sample pump (66);

a carrier liquid containing vessel (70) connected to said switch-over valve (62);

the sample pump (66) constituting a single pump which is selectively connected through said switch-over valve (62) either to said vessel (70) containing carrier liquid or the dosing needle (20).

11. Dosing device as set forth in claim 1, wherein:

said tapered sealing surface (138) formed at the front end (137) of said dosing needle (20) constitutes a substantially conically tapered sealing surface; and said annular shoulder (136) defined between said straight first section (130) and said second section (132) of said sample inlet passage (128) in said sealing body (108) of said change-over valve (24), having a substantially conically tapered configuration complementary to said substantially conically tapered sealing surface at said front end of said dosing needle.

* * * * *

UNITED STATES PATENT AND TRADEMARK OFFICE
CERTIFICATE OF CORRECTION

PATENT NO. : 5,194,226
DATED : March 16, 1993
INVENTOR(S) : Toma Tomoff, et. al.

It is certified that error appears in the above-indentified patent and that said Letters Patent is hereby corrected as shown below:

Column 2, line 60, after "Patent No. 30 30 396" insert --a change over--.
Column 7, line 43, change "second" to --first--
Column 8, line 14, delete "56 inlet" and insert --inlet 56--
Column 12, line 64, after "(132)" insert --communicating with said straight first section 130 and --.
Column 14, line 8, delete "a sensor"and insert -- an actuating--.

Signed and Sealed this

First Day of February, 1994

Attest:

BRUCE LEHMAN

*Attesting Officer*   Commissioner of Patents and Trademarks